(12) United States Patent
Stürzl et al.

(10) Patent No.: US 7,498,144 B2
(45) Date of Patent: Mar. 3, 2009

(54) ELISA METHOD FOR THE DETECTION OF GUANYLATE BINDING PROTEIN 1 (GBP-1)

(75) Inventors: Michael Stürzl, Erlangen (DE); Clara Lubeseder-Martellato, Munich (DE); Eric Guenzi, Dachau (DE); Elisabeth Kremmer, Freising (DE)

(73) Assignee: Helmholtz Zentrum Munchen Deutsches Forschungszentrum fur Gesundheit und Umwelt (GmbH), Neuherberg (DE)

( * ) Notice: Subject to any disclaimer, the term of this patent is extended or adjusted under 35 U.S.C. 154(b) by 0 days.

(21) Appl. No.: 10/537,607

(22) PCT Filed: Dec. 19, 2003

(86) PCT No.: PCT/EP03/14678

§ 371 (c)(1),
(2), (4) Date: Oct. 7, 2005

(87) PCT Pub. No.: WO2004/057339

PCT Pub. Date: Jul. 8, 2004

(65) Prior Publication Data

US 2006/0154316 A1 Jul. 13, 2006

(30) Foreign Application Priority Data

Dec. 20, 2002 (DE) .............................. 102 60 265

(51) Int. Cl.
*G01N 33/537* (2006.01)
*G01N 33/53* (2006.01)

(52) U.S. Cl. .................................................. 435/7.92

(58) Field of Classification Search ........................ None
See application file for complete search history.

(56) References Cited

U.S. PATENT DOCUMENTS 6,894,157 B2 * 5/2005 Sturzl et al. ................ 536/24.3
2002/0115138 A1 8/2002 Sturzl et al.

OTHER PUBLICATIONS

Lubeseder-Martellato et al., American Journal of Pathology, vol. 161, No. 5, Nov. 2002, pp. 1749-1759.
Guenzi et al., EMBO Journal, Oxford University Press, Surrey, GB, vol. 20, No. 20, Oct. 15, 2001, pp. 5568-5577.
Yih et al., Journal of Biological Chemistry, American Society of Biological Chemists, Baltimore, MD, US, vol. 258, No. 12, Jun. 23, 1983, pp. 7746-7750.
Strehlow et al., Gene, vol. 144, No. 2, 1994, pp. 295-299.
P. Carmeliet et al., Nature vol. 407, Sep. 14, 2000, pp. 249-257.
J. Folkman, Nature Medicine, vol. 1, No. 1, 1995, pp. 27-31.
E. Guenzi et al., The EMBO Journal, vol. 22, No. 15, 2003, pp. 3772-3782.
H.B. Lowman, Annu. Rev. Biophys. Biomol. Struct., vol. 26, 1997, pp. 401-424.
B. Prakash et al., Nature, vol. 403, Feb. 3, 2000, pp. 567-571.
K. Topolt et al., 22nd Meeting of the European Society for Microcirculation Exeter, United Kingdom, Aug. 28-30, 2002, pp. 215-219.

* cited by examiner

*Primary Examiner*—Robert Landsman
*Assistant Examiner*—Ian Dang
(74) *Attorney, Agent, or Firm*—Birch, Stewart, Kolasch & Birch, LLP

(57) ABSTRACT

A method for the identification and/or quantification of GBP-1 or fragments of this protein in the culture supernatant of a tissue sample, a body fluid sample or a sample from a cell culture supernatant is described.

21 Claims, 9 Drawing Sheets

Secretion of GBP-1 from INF-γ-treated HUVEC is not based on an increase in apoptosis and/or cell permeability

ELISA METHOD FOR THE DETECTION OF GUANYLATE BINDING PROTEIN 1 (GBP-1)

The present invention relates to methods for the identification and/or quantification of GBP-1 or fragments of this protein in the culture supernatant of a tissue sample, a body fluid sample or a sample from a cell culture supernatant.

Various documents are cited in the text of this description. The disclosure content of the cited documents (including all the manufacturers' instructions, information, and so on) is thus, as reference, part of this description.

The endothelium is a key organ in numerous physiological and pathophysiological processes such as cell-directed immune response, menstruation, wound healing, inflammation, allergy, cardiovascular disease and tumour growth. The pathofunction of the endothelium is inseparably linked to the activation of endothelial cells.

Figure 1:
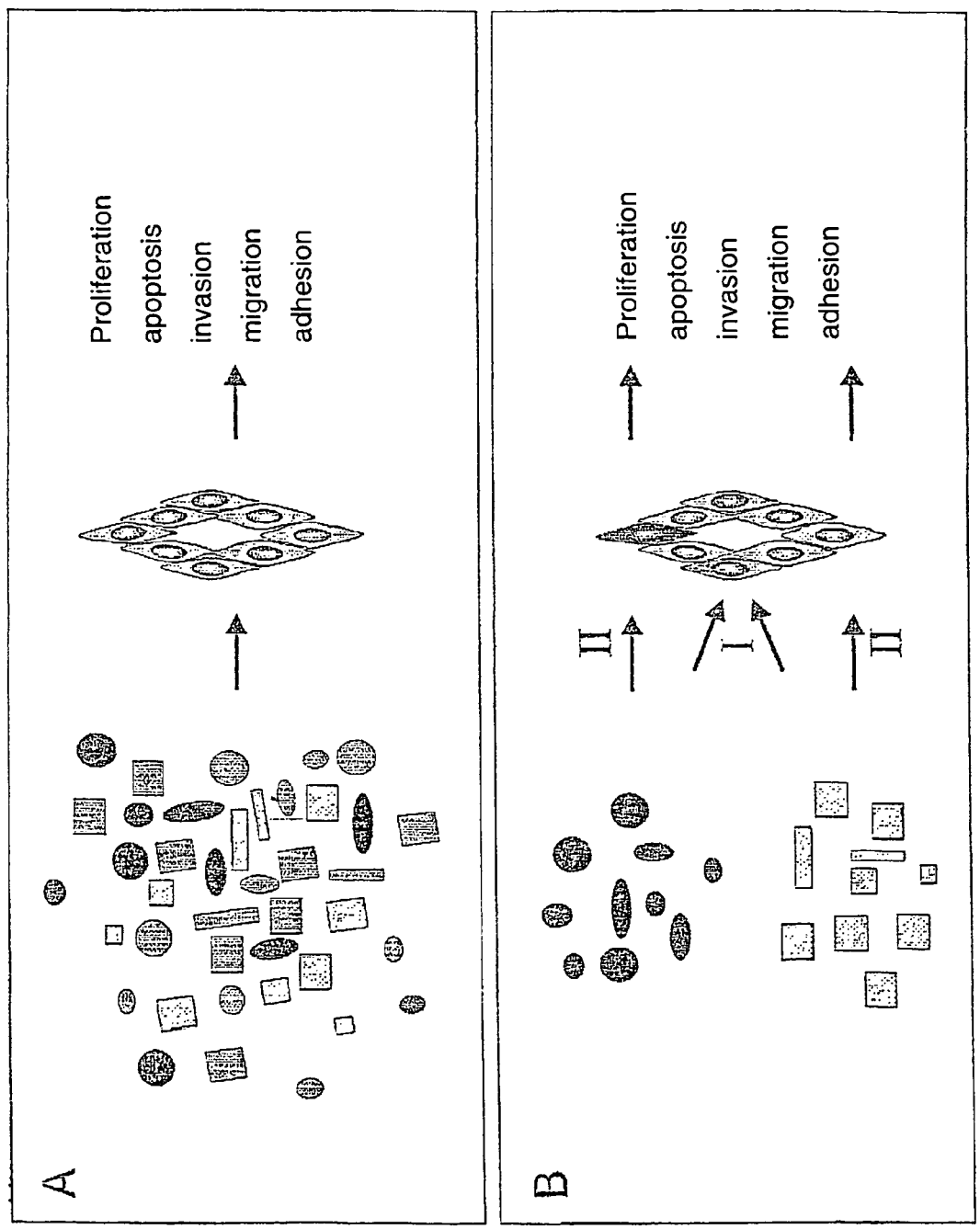

The activation of the endothelium is a complex process which is controlled by a plurality of various soluble factors which circulate in the blood or which are released by neighbouring cells (FIG. 1A). This process results in the physiology and the morphology of the endothelial cells being adjusted to the relevant requirements in the tissue. In this context, the factors of main importance are the control of the cell proliferation, apoptosis, invasion, migration and the leukocyte adhesion capacity of endothelial cells, by means of which the regeneration and degeneration of vessels and the extravasation of leukocytes are regulated (FIG. 1A).

The plurality of factors involved suggests that several factors control the same phenotype and can be summarised in groups which have the same effects (FIG. 1B). The angiogenic growth factors basic fibroblast growth factor (bFGF) and vascular endothelial cell growth factor (VEGF), for example, activate the endothelial cell proliferation, whereas the inflammatory cytokines interleukin (IL)-1α, IL-1β, tumour necrosis factor (TNF)-α and interferon (IFN)-γ inhibit proliferation and increase the leukocyte adhesion capacity of endothelial cells.

At present, there are no suitable methods by which it can be determined where and when the different factors have an effect on the endothelial cells in inflammatory tissues. Therefore, with regard to inflammatory diseases, only very little is known about the distribution as to space and time of the different activation conditions of the endothelial cells.

The development of inflammatory reactions and the resulting inflammatory diseases is a very complex sequence (cascade) of different and synergistic effects of inflammatory factors such as cytokines which make an analysis of a defined stadium of an inflammatory reaction and/or a reliable prediction as to its further development hardly possible. Due to this complexity of the reactions taking place, in this context, one also speaks of a so-called cytokine network.

First efforts identifying a molecular marker which shows an activation of the endothelial cells by means of the above-mentioned inflammatory cytokines in the tissue led to comparative studies of gene expression in cultivated endothelial cells under different activation conditions. By this approach, a gene could be isolated the expression of which in endothelial cells is selectively induced by inflammatory cytokines (FIG. 2A) (Guenzi et al., 2001; Lubeseder-Martellato et al. 2002). This gene encodes the guanylate binding protein-1 (GBP-1) which belongs to the protein family of the big GTPases.

Figure 2:
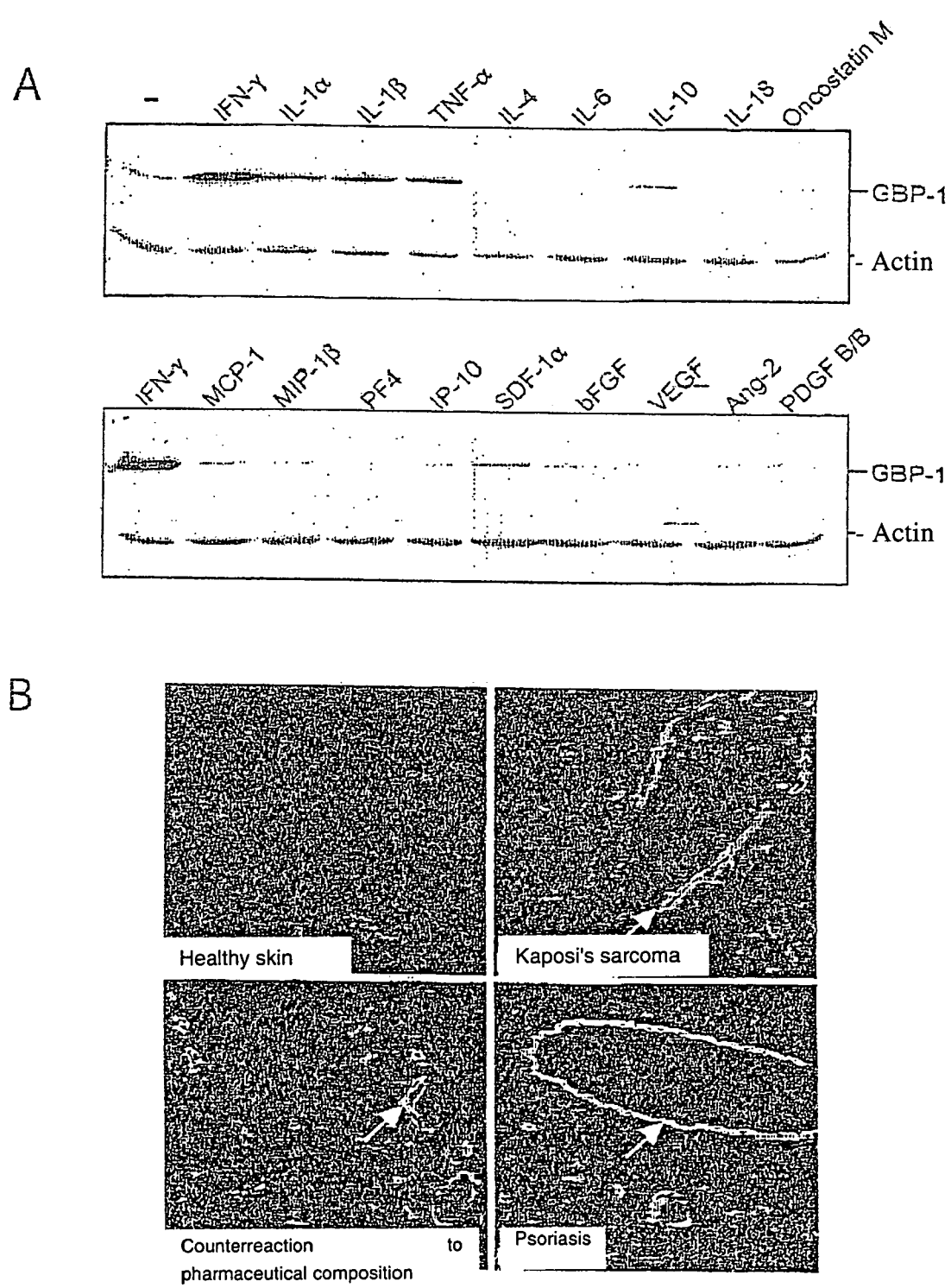

In order to determine whether GBP-1 also shows an activation by means of inflammatory cytokines in vessel endothelial cells in human tissues—as it does in cultivated cells—immunohistochemical analyses were carried out for the detection of GBP-1 by means of specific monoclonal antibodies. For this purpose, histological sections of healthy skin and of skin diseases with an inflammatory component, such as psoriasis, counter reaction to pharmaceutical compositions and Kaposi's sarcoma were analysed (FIG. 2B). All the skin diseases mentioned have in common that in the lesions, numerous inflammatory cells are present in a focally concentrated manner, which release the same inflammatory cytokines that also lead to an increased GBP-1 expression. In the vessels of healthy skin GBP-1 could not be detected in any case. In contrast, in all the inflammatory diseases examined, individual vessels were clearly positive for GBP-1 (FIG. 2B, arrows). These results showed that, in fact, GBP-1 shows an inflammatory activation of endothelial cells in human tissues, too, and can be used as molecular marker for the detection of this activation in tissues (Lubeseder-Martellato et al. 2002, Guenzi et al. 2001). This use as molecular marker was, however, limited to solid tissue samples, since the described results showed that the protein GBP-1 is a protein which is effective in the cell and which is located in the cytoplasma of the cell. Therefore, relevant detections comprised e.g. obtaining solid tissue samples from patients. Taking solid tissue samples from inflammatory tissue has, however, disadvantageous effects for the patients and is difficult.

Figure 3:
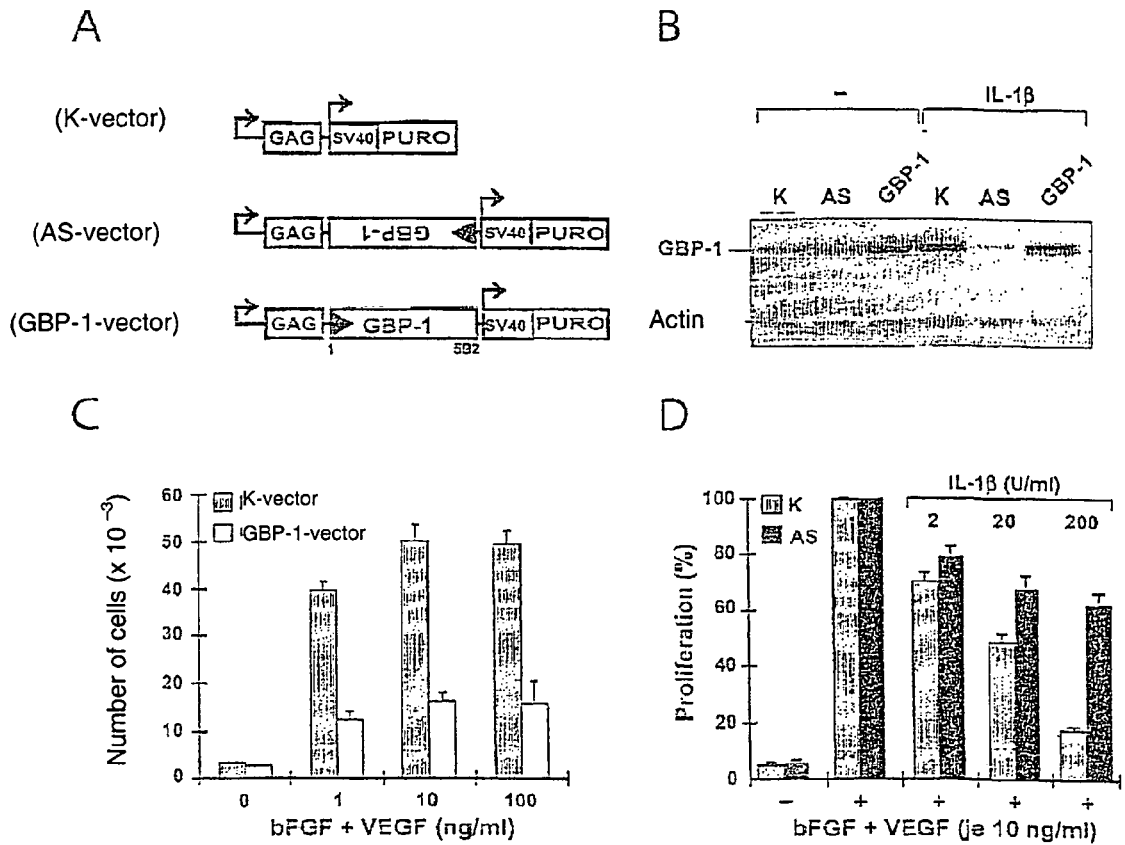

In endothelial cells, the induction of the GBP-1 expression by inflammatory cytokines means an inhibition of the cell proliferation. Thus, it was examined whether GBP-1 mediates the proliferation inhibition induced by inflammatory cytokines. For this purpose, endothelial cells were transduced with retroviral vectors which cause the constitutive expression of GBP-1 (GBP-1 vector) or an antisense GBP-1 RNA (AS vector) (FIG. 3A). Western blot analyses confirmed that endothelial cells that were transduced with the GBP-1 vector expressed GBP-1 very strongly (FIG. 3B). In cells that were transduced with the AS vector, the induction of the GBP-1 expression by IL-1β was efficiently blocked (FIG. 3B). Subsequent proliferation experiments with the different transduced cell cultures showed that GBP-1, in fact, inhibits the cell proliferation induced by angiogenic growth factors (FIG. 3C, white bars) and, furthermore, is necessary for inflammatory cytokines being able of inhibiting the proliferation of endothelial cells (FIG. 3D). The last fact can be seen from the fact that in cell cultures expressing antisense GBP-1 RNA, the inhibitory effect of inflammatory cytokines on cell proliferation is clearly reduced (FIG. 3D, black bars) (see Guenzi et al., 2001).

Moreover, GBP-1 inhibits the expression of matrix metalloproteinase-1 and, therefore, the invasion of endothelial cells (see Guenzi et al., 2003).

More detailed analyses as to structure/function relations of GBP-1 showed that, interestingly, the adhesion capacity of endothelial cells for leucocytes, which is also induced by inflammatory cytokines, is not influenced by GBP-1 (Guenzi et al., 2001). GBP-1 is, thus, a new molecular marker for an inflammatory tissue activation, which selectively controls the antiproliferative effect of inflammatory cytokines on endothelial cells.

So far, it could be shown that GBP-1 is selectively induced by inflammatory cytokines and that this process correlates with an anti-angiogenic effect on the cells concerned (Lubeseder-Martellato et al., 2002 and Guenzi et al., 2001). Whereas one could, in principle, take advantage of the induction of GBP-1 through its anti-proliferative effect for medicinal purposes in form of an anti-angiogenic therapy, the use of inflammatory cytokines for such purposes is out of question due to the pleiotropic and therefore also disadvantageous effects of these cytokines.

Despite the fact that there is a need for suitable molecular markers for inflammatory diseases, in the prior art, numerous cytokines and factors participating in the formation and the development of inflammatory diseases are described as unsuitable for this purpose due to their instability. Furthermore, a quantification of individual inflammatory cytokines or factors is not sufficient for a clear result and, therefore, requires the determination of a vast number of different cytokines and factors which each show their effect in a so-called "cytokin network" only.

Thus, the problem of the present invention was the provision of a method allowing for a simple and direct analysis of the expression of GBP-1. This method is supposed to allow statements on the stadium and progress of an inflammatory reaction in an individual or in an in vitro model without time-consuming and costly analyses and quantification of many different inflammatory factors of the so-called cytokin network being necessary.

This problem has been solved by the provision of the embodiments characterised in the claims.

Therefore, the present invention relates to an in-vitro method for the identification and/or the quantification of GBP-1 or of fragments of this protein in the culture supernatant of a tissue sample, a sample of body fluid or a sample of a cell culture supernatant, wherein the method comprises the following steps:

(a) contacting of the sample with a first receptor which specifically binds GBP-1 or a fragment of this protein; and
(b) detection of a specific binding of the receptor with GBP-1 or a fragment of this protein.

In the context of the present invention, the term "fragment of GBP-1" preferably describes both the fragments of this protein which have the biological activity of GBP-1 as described in the prior art and in this application, and fragments of the protein, which occur by cleavage, e.g. enzymatic cleavage, and which are indicative for inflammatory diseases.

In the context of the invention, the term "body fluids" comprises all kinds of body fluids, optionally diluted or concentrated. Examples are blood/serum, plasma, amniotic fluid, brain/spinal cord fluid, liquor, cerebrospinal fluid, sputum, throat and pharynx secretions and other mucous membrane secretions, synovial fluids, ascites, tear fluid, lymph fluid and urine.

According to the invention, the term "specific binding" describes a specific interaction between a receptor and a ligand. One example of such a ligand is GBP-1 or fragments of this protein. The specific interaction can be characterised with a "key-lock-principle". The receptor and the ligand have structures or motifs which fit with each other specifically, as e.g. an antigenic determinant (epitope) which interacts with the antigen binding site of an antibody. Accordingly, specific interaction is contrary to a more universal, more unspecific interaction.

It was shown that GBP-1 is a maker protein for inflammatory reactions which surprisingly, is secreted, inter alia, by endothelial cells and monocytes. This surprising result makes it possible to analyse GBP-1 in the culture supernatant of tissue samples, samples of body fluids or samples of cell culture supernatants and to make a statement about the stadium of an inflammatory disease. By means of the method according to the invention, secreted GBP-1 can be detected in a simple and fast manner and, thus, serves as disease-associated diagnostic parameter.

On the basis of the surprising result, the detection of an inflammatory activation of endothelial cells and monocytes in the body fluid of patients by means of the method according to the invention is particularly important with respect to inflammatory diseases, bacterial and viral infectious diseases (AIDS, meningitis), allergies, transplant reactions, cardiovascular and tumour diseases and so on. Furthermore, these are important for the determination of the response reaction with patients under treatment with inflammatory cytokines (e.g. interferon-$\alpha$); see FIG. 5.

The detection or the quantified amount of GBP-1 in a sample of a body fluid of a patient allows conclusions to be drawn as to activation level of endothelial cells and monocytes and, thus, a statement about the clinical picture of the patient.

Methods for obtaining the samples mentioned are known to the person skilled in the art. Optionally, the method according to the invention, moreover, comprises one or several washing steps prior to or after each method step. These washing steps serve the minimisation of unspecific reactions (false positive or false negative detection) and can improve the sensitivity of the method.

Suitable washing buffers and their composition are, in principle, known to the person skilled in the art; see e.g. Harlow and Lane. Physiological buffer solutions are preferred.

A preferred embodiment of the method according to the invention, moreover, comprises step (a') or (a") prior to contacting with the first receptor:

(a') labelling of the proteins contained in the sample; or
(b') labelling of the first receptor.

The proteins contained in the sample and/or the first receptor can, for example, be labelled chemically, e.g. by coupling of labelled chemical groups or markers to free amino groups of cysteines contained in the proteins. Examples of such marked chemical groups are groups containing special, detectable radioisotopes. For example fluorescent dyes can also serve as markers. A further example of appropriate markers are nucleic acids. The presence of proteins or receptors in a sample which are labelled in such a way can then be detected with suitable primers in a polymerase chain reaction (PCR).

Furthermore, it is possible to label proteins physiologically, i.e. by the metabolic integration of labelled molecules. For this purpose, cells are, for example, incubated with radioactively labelled metabolites. Proteins originating from the biosynthesis of these cells during this incubation period and in which the labelled metabolites were integrated are marked. This method is e.g. suitable to label antibodies secreted by cells which produce antibodies.

In a further preferred embodiment of the method according to the invention, the receptor is immobilised on a surface prior to contacting with GBP-1 or fragments of this protein.

According to an alternative embodiment of the method of the invention, the receptor is immobilised on a surface after contacting with GBP-1 or fragments of this protein. Receptors can be immobilised in various way. The appropriate method depends on various factors, such as e.g. the type of receptor or the material of the surface. An immobilisation can take place covalently or by adsorption. According to a preferred embodiment of the method according to the invention, the receptors are proteins, particularly preferred antibodies. Also preferred is the use of peptides or organic molecules as receptors.

For the immobilisation of receptors which are proteins, methods are described in which the receptors are immobilised directly on a surface by means of passive adsorption. Normally, an appropriate surface consists of a polymer plastic material (e.g. polystyrene, polyvinyl, latex) and e.g. in form of microtitre plates or multi-well plates, membranes or spheric "beads" (cross-linked polymers in particle form) are used for this purpose (Lowman, *Annu. Rev. Biophys. Biomol. Struct.* 26 (1997), 401-24).

In a further preferred embodiment of the method according to the invention, the material of the surface is selected from the group consisting of sepharose, latex, glass, polystyrene, polyvinyl, nitrocellulose and silicon.

Further preferred, the surface in the method according to the invention is a membrane, a bead, a chip or a plate.

Examples of beads are sepharose beads or latex beads, to which, optionally, ligands are bound, which promote the immobilisation of the receptors to the surface. Such ligands are, for example, protein A or protein G which promote a binding of antibodies to a surface via the Fc part of the antibody. The binding of the receptor to a carrier material can also be achieved by a covalent chemical coupling reaction (e.g. hydrazide coupling). Example 3 describes a corresponding method. Another example of the immobilisation of the receptors to the surface by means of ligands is the use of biotin and avidin or streptavidin.

Examples of chips are silicon plates onto which a plurality of different or the same receptors can be immobilised systematically. This allows the analysis of a plurality of different parameters in a sample or the analysis of a plurality of different samples as to one or several parameters, e.g. identification and/or quantification of GBP-1 or fragments of this protein in different tissue samples, samples of body fluid or samples of cell culture supernatants.

Examples of the plates mentioned are microtitre plates or multi-well plates. Preferably, these have 6, 12, 24, 48, 96, 128, 356, 1024 or more wells. In Example 4, a method is described wherein 96-well plates are used.

According to a further preferred embodiment of the method, it further comprises step (a''') prior to the step of detection of a specific binding:

(a''') Precipitating the beads with the complexes of the first receptor and GBP-1 or a fragment of this protein which are bound thereto.

Beads can be precipitated from a sample e.g. in a gravimetric manner. This can be accelerated, for example, by centrifugation. Appropriate methods are known to the person skilled in the art, amongst others from Rehm, Der Experimentator: Proteinbiochemie/Proteomics, Spektrum Akademischer Verlag, 2002. Furthermore, an appropriate precipitation is described in Example 3.

In a further preferred embodiment of the method according to the invention, the detection of the specific binding in step (b) comprises a gel electrophoretic cleavage, optionally, furthermore, a Western blot analysis (cf. Example 3). Appropriate methods are known to the skilled person, among others from Rehm, loc. cit.

In a further preferred embodiment of the method according to the invention, the detection of a specific binding of GBP-1 or a fragment of this protein with the first receptor in step (a), the sample is contacted with a second receptor for GBP-1 or a fragment of this protein, which binds with an epitope of GBP-1 or a fragment of this protein, which is accessible after binding of the first receptor with GBP-1 or a fragment of this protein.

This preferred embodiment relates, for example, to methods taking advantage of the mechanistic principle of the sandwich ELISA. This principle is generally known to the person skilled in the art and is described, amongst others, in Stryer, Biochemie, Spektrum Akademischer Verlag, 1996. Furthermore, a corresponding method is described in the enclosed Example 4.

Furthermore, in a preferred embodiment of the method of the invention, the second receptor for GBP-1 or fragments of this protein is labelled. Methods allowing labelling of a receptor have been described above and can be used here, too.

Moreover, it is preferred that the labelling of the second receptor for GBP-1 or a fragment of this protein comprises a system emitting a signal. Also preferred is a specific recognition of the labelling by means of another, third receptor comprising a system emitting a signal.

An example of such system emitting a signal is the above-described isotope labelling, wherein the signal is the release of radioactive radiation. Likewise, fluorescent labelling of the corresponding receptor results in the labelling with a system emitting a signal according to the invention, wherein the signal is the emission of a fluorescence signal after appropriate stimulation of the dye.

According to the invention, further preferred, the system emitting a signal comprises an enzyme emitting a signal. Examples of such enzymes comprise alkali phosphatases, peroxidases, β-galactosidase, glucoamylase, urease and chloramphenicol acetyltransferase. Appropriate examples and the use of necessary substrates for the detection by means of enzymatic reactions are known to the person skilled in the art, amongst others from the package leaflet of commercially available detection kits or from Rehm, loc. cit. Such commercially available kits often contain antibodies which recognise the antibodies of specific species, e.g. anti-mouse, and to which enzymes emitting signals are coupled. Thus, corresponding antibodies are examples of the third receptor, which recognise a specific labelling of the second receptor, that is its Fc part.

In another preferred embodiment of the method according to the invention, the first and the second receptor and, optionally, also the third receptor, are selected from the group consisting of peptides, polypeptides, low-molecular substances, antibodies or fragments or derivatives thereof and aptamers.

The term peptides usually refers to amino acid chains with up to 30 amino acids.

The term polypeptides refers to peptides which usually comprise more than amino acid chains 30 amino acids and includes proteins.

The term "low-molecular substances" or small molecules refers to molecules which are of low-molecular complexity than the macro molecules defined above. In the literature, the term "low-molecular substances" is not used in a uniform manner. In WO 89/03041 and WO 89/03042, molecules with a molecular mass of up to 7000 g/mol are described as small molecules. Usually, however, molecular masses between 50 and 3000 g/mol, more often, however, between 75 and 2000 g/mol and mostly in the range between 100 and 1000 g/mol are stated. Examples are known to the person skilled in the art from the documents (WO86/02736, WO97/31269, U.S. Pat. No. 5,928,868, U.S. Pat. No. 5,242,902, U.S. Pat. No. 5,468, 651, U.S. Pat. No. 5,547,853, U.S. Pat. No. 5,616,562, U.S. Pat. No. 5,641,690, U.S. Pat. No. 4,956,303 and U.S. Pat. No. 5,928,643. Low-molecular substances can be of organic or inorganic nature.

According to the invention, the term "antibody" comprises polyclonal sera as well as monoclonal antibodies.

Monoclonal antibodies and methods for the production thereof are known to the person skilled in the art. These are based on a method first described by Köhler and Milstein (1975). This method is described in detail in, amongst others, the laboratory manual by Harlow and Lane (Antibodies, A laboratory manual; Cold Spring Harbor Laboratory; (1988); Chapter 6). By this definition, bispecific antibodies, synthetic antibodies and fragments or derivative of these antibodies are also comprised. These comprise fragments such as Fab, Fv or scFv and chemically modified derivatives of these antibodies or antibody fragments.

Aptamers are, in principle, known to the person skilled in the art from prior art. Preferably, the method according to the invention is an ELISA, an EIA or a RIA. Appropriate methods are, in principle, known to the person skilled in the art from Harlow and Lane, loc. cit. and Rehm, loc. cit.

The method according to the invention is preferably carried out automatically. This is possible, amongst others, by the use of pipetting robots and for an automated analysis of optimised processes.

Furthermore, the invention refers to the use of body fluids or a sample of a cell culture supernatant, as defined above, for the detection of GBP-1 or of fragments of this protein, wherein the positive detection is indicative for the presence of an inflammatory disease.

Further (preferred) embodiments of the use according to the invention correspond to those of the method described above.

The figures show:

FIGS. 1A-B: Complexity and redundancy of inflammatory endothelial cell activation.

(A) The activation of the endothelium with inflammatory processes is controlled by a plurality of different soluble factors from the blood and from neighbouring cells. Regarding the regeneration and the degeneration of vessels and the extravasation of leucocytes, the control of cell proliferation, apoptosis, invasion, migration and the ability for adhesion for leucocytes are most important.

(B) The large number of factors involved leads to the assumption that several factors influence the same activation and can be bundled into groups which have the same effects. At present, it is not possible to determine when and where the different factors have an influence on the individual endothelial cells. Moreover, the relations of most activation types to one another are mostly unknown. It has to be determined whether all activations can occur simultaneously in a cell (I) or whether they have to be separated regarding time and space due to restrictions of cellular biological nature (II).

FIGS. 2A-B: Expression of GBP-1 in cultivated endothelial cells and in inflammatory skin diseases.

(A) Western blot analysis of GBP-1 expression in endothelial cells which had been stimulated with the indicated factors for 24 h. The following concentrations were used: IFN-γ (100 U/ml), IL-1α (5 ng/ml), IL-1β (200 U/ml), TNF-α (300 U/ml), IL-4 (10 U/ml), IL-6 (50 U/ml), IL-10 (50 ng/ml), IL-18 (100 ng/ml), oncostatin M (10 ng/ml), MCP-1 (50 ng/ml), PF4 (25 ng/ml), SDF-1α (200 ng/ml), bFGF (10 ng/ml), VEGF (10 ng/ml), Ang-2 (800 ng/ml) and PDGF B/B (100 ng/ml). The simultaneous detection of the cytoskelettal protein actin shows that the same amounts of proteins were applied.

(B) Induction of the GBP-1 expression in vascular endothelial cells in skin diseases with an inflammatory component. Indirect immunofluorescence staining of GBP-1 (green) and of the endothelial cell-associated antigen CD31 (red) in the tissue section of healthy skin, Kaposi's sarcoma, inflammatory counterreaction to pharmaceutical preparation of the skin and psoriasis. The superposition of the pictures shows a co-expression (yellow) of GBP-1 and CD31 (white arrows). (Modified on the basis of (Lubeseder-Martellato, Guenzi et al., 2002))

FIGS. 3A-D: GBP-1 mediates the antiproliferative effect of inflammatory cytokines in endothelial cells (A) Schematic representation of the retroviral expression vector pBabePuro (control vector, K-vector) into which the cDNA of GBP-1 was inserted in both orientations for the constitutive expression of GBP-1 (GBP-1-vector) and for the expression of a GBP-1-antisense-RNA (AS-vector).

(B) GBP-1 expression in K-, GBP-1-, and AS-vector transduced endothelial cells, which were either untreated or were stimulated over a period of 24 h with 20 U/ml IL-1β. The detection of the GBP-1 expression was carried out by means of Western blot analysis with a polyclonal anti-GBP-1 antibody. The simultaneous staining with actin showed that the same amounts of proteins were applied.

(C) Proliferation experiments with K-vector- and GBP-1-vector-transduced endothelial cells in the presence of increasing concentrations of angiogenic growth factors (bFGF and VEGF in combination).

(D) Proliferation experiments of K-vector and AS-vector-transduced endothelial cells in the presence of angiogenic growth factors and an increasing concentration of IL-1β. (Modified on the basis of (Guenzi, Topolt et al., 2001)).

Figure 4:
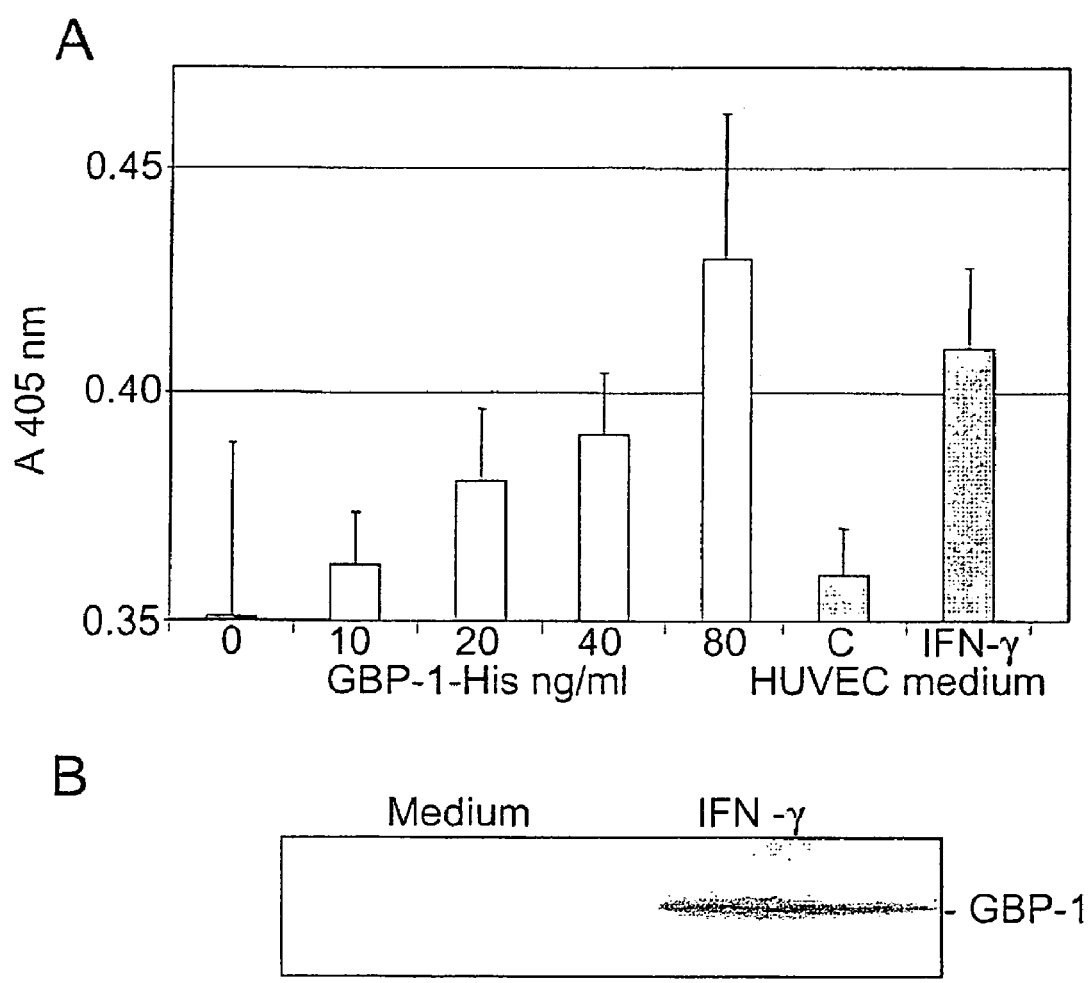

FIGS. 4A-B: Detection of GBP-1 protein in culture medium of IFN-γ stimulated HUVEC by ELISA and immunoprecipitation HUVEC were stimulated with 100 U/ml IFN-γ (IFN-γ) or were left untreated (medium). After culturing for 24 hrs, the culture medium was analysed with ELISA (A) or immunoprecipitation (B).

(A) A dilution series with recombinant purified GBP-1 was used as standard (white columns). The amount of secreted GBP-1 protein was determined by means of ELISA (grey columns). The absorption was determined at 405 nm.

(B) Western blot analysis of immunoprecipitated human GBP-1 protein with monoclonal anti-GBP-1 antibody (clone 1B1) from the same culture supernatant as in (A).

Figure 5:
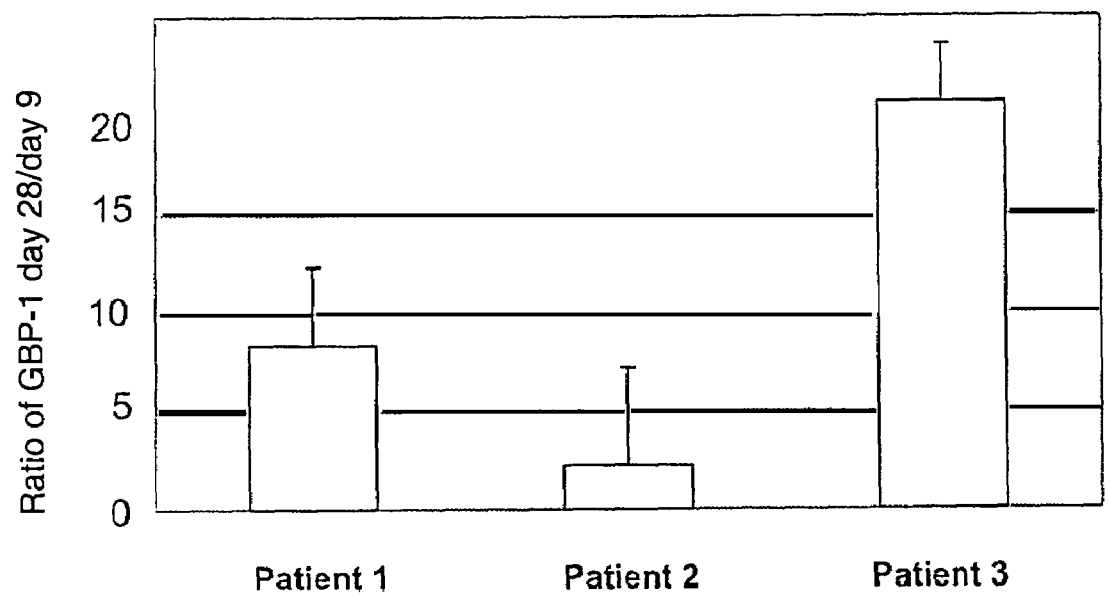

FIG. 5: Measuring circulating GBP-1 in the plasma of patients treated with IFN-α

The concentration of circulating GBP-1 in the plasma was determined by means of ELISA in patients suffering from a melanoma who had been treated with IFN-α for 9 or 28 days. The increase of the GBP-1 concentration is shown from day 9 to day 28 in three patients. ELISA microtitre plates were coated with a monoclonal rat-anti-GBP-1 antibody, clone 1B1 for 16 hrs at 4° C. Subsequently, the plates were with PBS-T (0.1% Tween 20 in PBS) and for 30 minutes, free binding sites were saturated with PBS-T/BSA 2% (PBS-TB) at room temperature (RT). After sucking off the PBS-TB, an incubation followed (2 hrs) with 100 μl of different plasma samples (1:2), each, at room temperature. Purified GBP-1 His protein, diluted in cell culture medium (EMB-0.5% FCS) was used as standard. BSA served as negative control. The samples were washed 4 times with PBS-T, in each case 100 μl polyclonal rabbit-anti-GBP-1 antibody (1:500) was added and incubated for 2 hrs at room temperature. After washing four times with PBS-T, an incubation followed (1 hr, room temperature) with 100 μl, in each case, of AP-conjugated anti-rabbit antibody (1:500) diluted in PBS-TB). After another four washing steps, the GBP-1 protein/antibody complex was visualised by incubation with 100 μl p-nitro phenyl phosphate. The absorption was measured at 405 nm in the micro plate reader. The determination of the concentration was carried out using a standard curve for which increasing concentrations of purified GBP-1-His were used. The linearity of the measurement is indicated for a range of 0.1 to 100 ng/ml.

Figure 6:
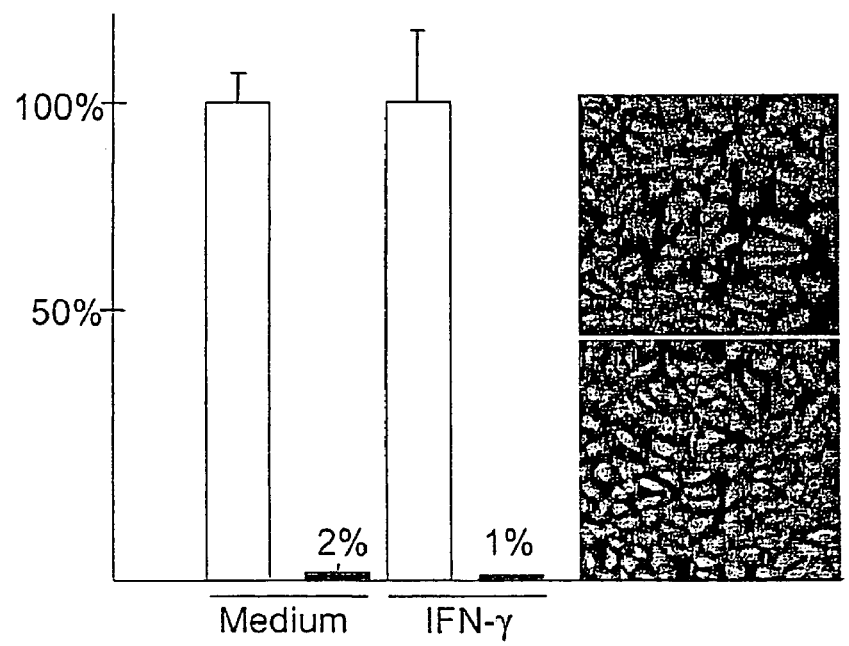

FIG. 6: The secretion of GBP-1 protein from IFN-γ-treated HUVEC is not due to an increasing permeability of cellular membranes or apoptosis The staining of HUVEC with the dye "Dead-Red" which is unable to penetrate the membrane (Molekular Probes).

HUVEC were cultured over night in 0.5% FBS-containing EBM medium and stimulated with 100 U/ml interferon-γ (IFN-γ, Roche). Control cells (medium) were left untreated. 24 hrs after the stimulation, the cells were stained with Dead-Red dye. Cells which show a changed membrane permeability (black bars) are indicated as percentage of the total count (white bars).

Figure 7:
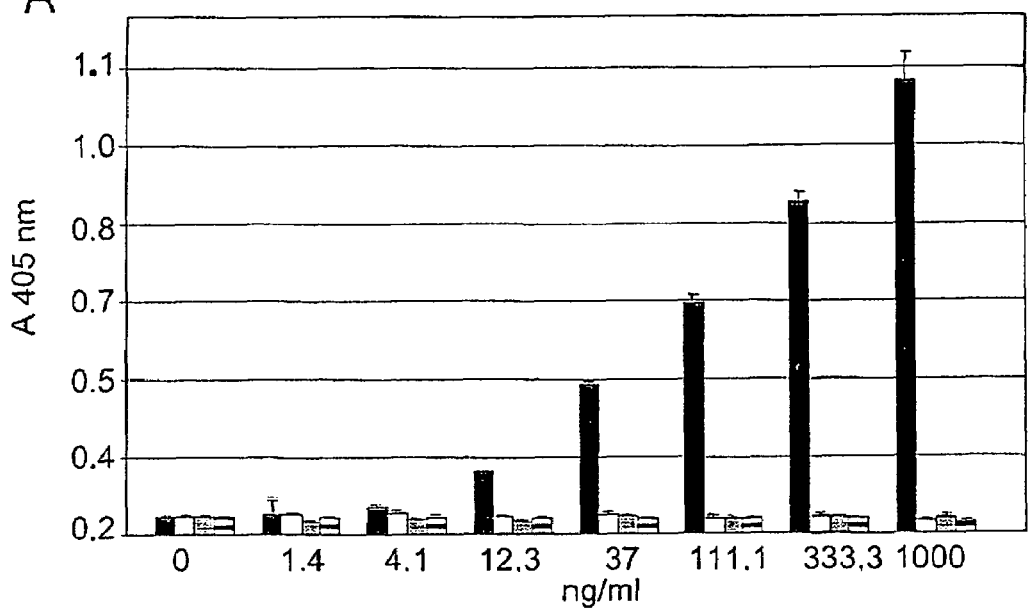
Figure 7:
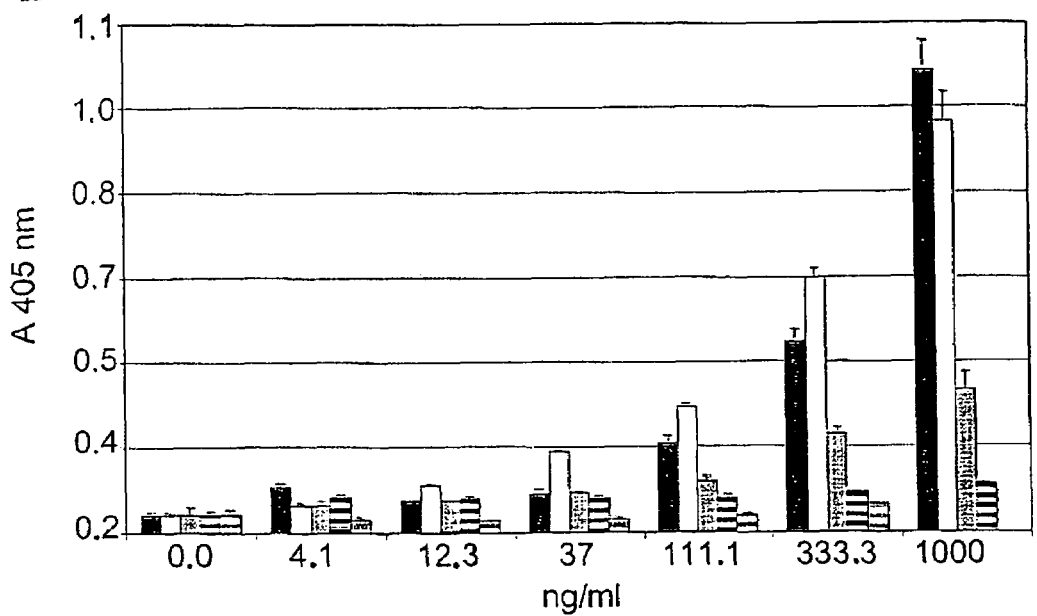

FIGS. 7A-B: The ELISA specifically reacts with GBP-1 and not with the heterologous proteins BSA and eGFP (A) The specificity of the GBP-1-ELISA was determined in several control experiments. First, a dilution series of purified GBP-1-His (a GBP-1 protein which was purified from bacteria and to which 6 histidine residues were added at the carboxy terminus for the purification) was produced in PBS at the indicated concentrations and measured in ELISA. In this context, a concentration-dependent increase of the absorption at 405 nm ($A_{405}$) is observed (black bars). If, instead of the anti-GBP-1-rabbit serum (used a second antibody for the detection of the bound GBP-1) a rabbit pre-immune serum is used, no signals were obtained (white bars). When adding increasing concentration of heterologous proteins [BSA (grey bars), His-eGFP (striped bars)] there were also no signals observed with the GBP-1-specific ELISA.

(B) The GBP-1-ELISA shows a low reactivity with GBP-1 homologous GBP-2.

With the GBP-1-ELISA solutions were examined containing increasing amounts of GBP-1-His (black bars), His-GBP-1 (white bars, a GBP-1 protein which was purified from bacteria and to which 6 histidine residues were added at the amino terminus for the purification) and His-GBP-2 [grey bars, a protein homologous to GBP-1 (homology at the amino acid level 76%, at the nucleic acid level 82%) with 6 histidine residues at the amino terminus]. The comparison of the increase in the measured values for GBP-1-His (black bars), His-GBP-1 (white bars) and His-GBP-2 (grey bars) showed that the reactivity of this ELISA with GBP-2 is reduced compared to the reactivity with GBP-1 and that the histidine residues at the amino or carboxy terminus do not influence the reactivity of the recombinant GBP-1.

Additionally, immunochemical blocking experiments were carried out in order to determine the specificity of the binding of purified GBP-1-His to the ELISA plate coated with rat-anti-GBP-1 antibodies. To this avail, GBP-1-His was incubated at different dilutions with (black and white bars) or without (black bars) rat-anti-GBP-1 antibody and subsequently put onto the plate. In the assays in which GBP-1-His was not preincubated with antibodies, a concentration-dependent increase in the signal strength was observed (black bar). However, the binding of GBP-1 to the surface of the plate could be blocked by pre-incubation with anti-GBP-1 antibodies (black and white bars). In an assay which was carried out in a comparable manner, also the binding of His-GBP-2 could be blocked by a pre-incubation with the rat-anti-GBP-1 antibody (grey and white bars).

Figure 8:
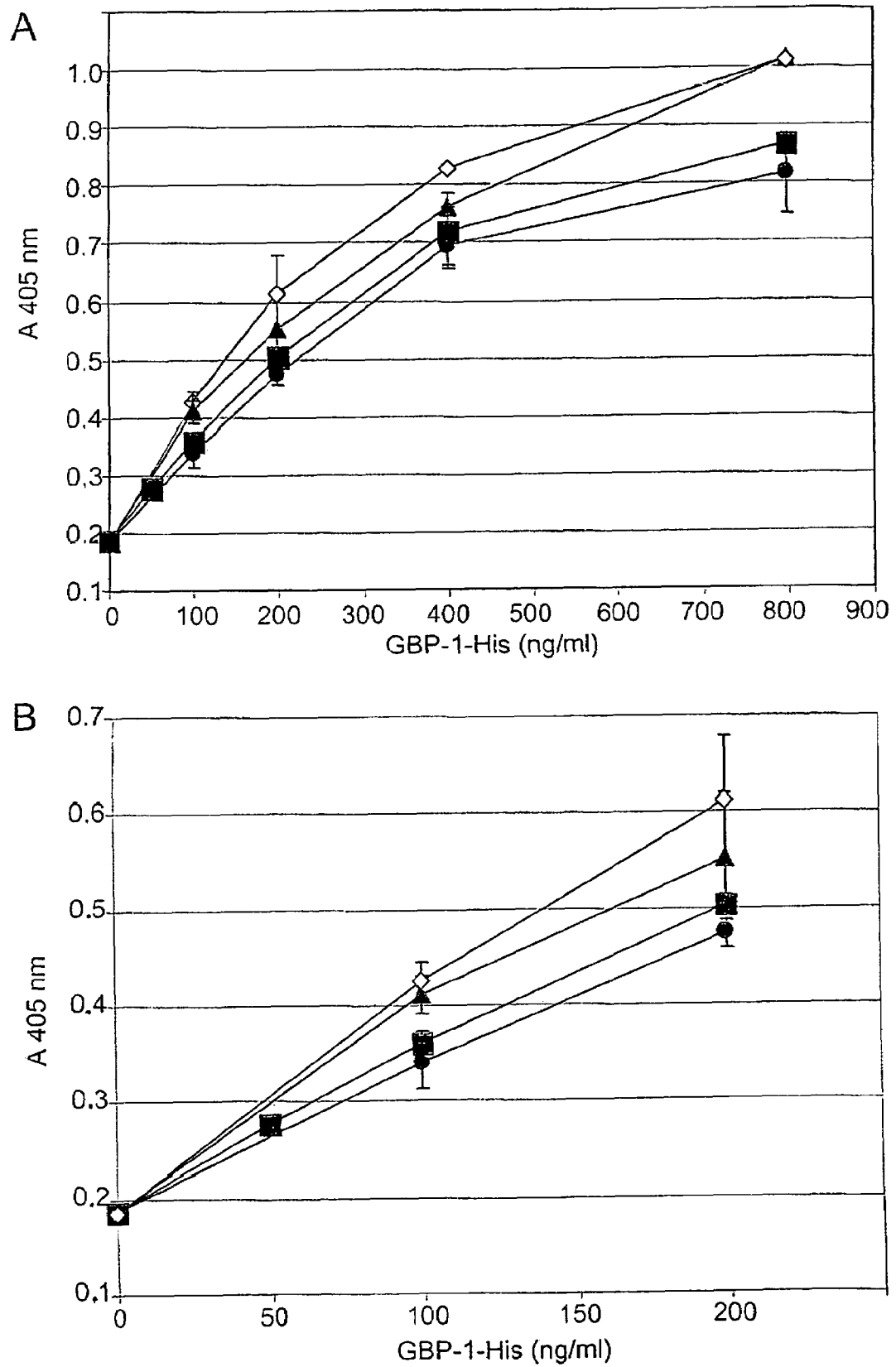

FIGS. 8A-B: Determination of the linear detection range of the ELISA (A) Pooled sera of healthy persons were diluted 1:2 (quadrangles), 1:4 (circles), 1:8 (triangles) and 1:16 (rhombs) in PBS/2% BSA. In each case increasing concentrations of GBP-1-His were added to the different dilutions. Subsequently, all samples were measured with a GBP-1-ELISA. The result was that in each of the different serum dilutions, the detection signals (A405) increased with the GBP-1 concentration.

(B) In the assay described under (A), a linear increase of the signal between 0 and 200 ng/ml was observed.

Figure 9:
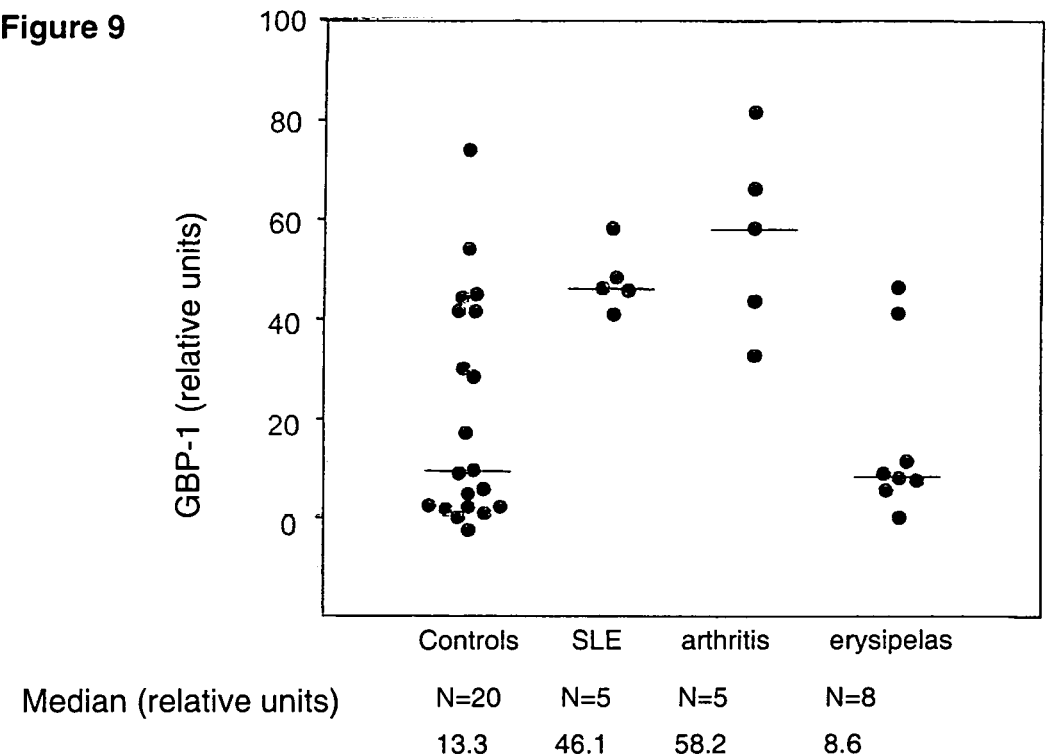

FIG. 9: Increased GBP-1 concentrations in the serum are detectable in patients with inflammatory diseases The GBP-1 concentration was measured by means of ELISA in healthy control persons (n=20) and in sera of patients with different inflammatory diseases (n=10): systemic lupus erythematosus (SLE) (n=5) and arthritis (n=5), these diseases are generalised inflammations, and in patients with erysipelas (n=8), a locally limited inflammation of the skin.

The GBP-1 serum concentrations were determined with the serum samples being diluted 1:2. The concentration of GBP-1 in the samples was calculated with the help of a standard curve. As the ELISA method also recognises GBP-2 and GBP-2 is possibly present in the serum, too, the determined concentrations were indicated in relative units.

The GBP-1 serum concentrations were markedly increased in the patients with SLE (median: 46.1 relative units) and arthritis (median: 58.2 relative units) but not in patients with erysipelas (median: 8.6 relative units) compared to the control persons (median: 13.3 relative units). The differences of the GBP-1 concentrations in patients with SLE and arthritis and the GBP-1 concentration in healthy control subjects is statistically significant (Wilcoxon Test $p<0.01$ for SLE and arthritis).

Figure 10:
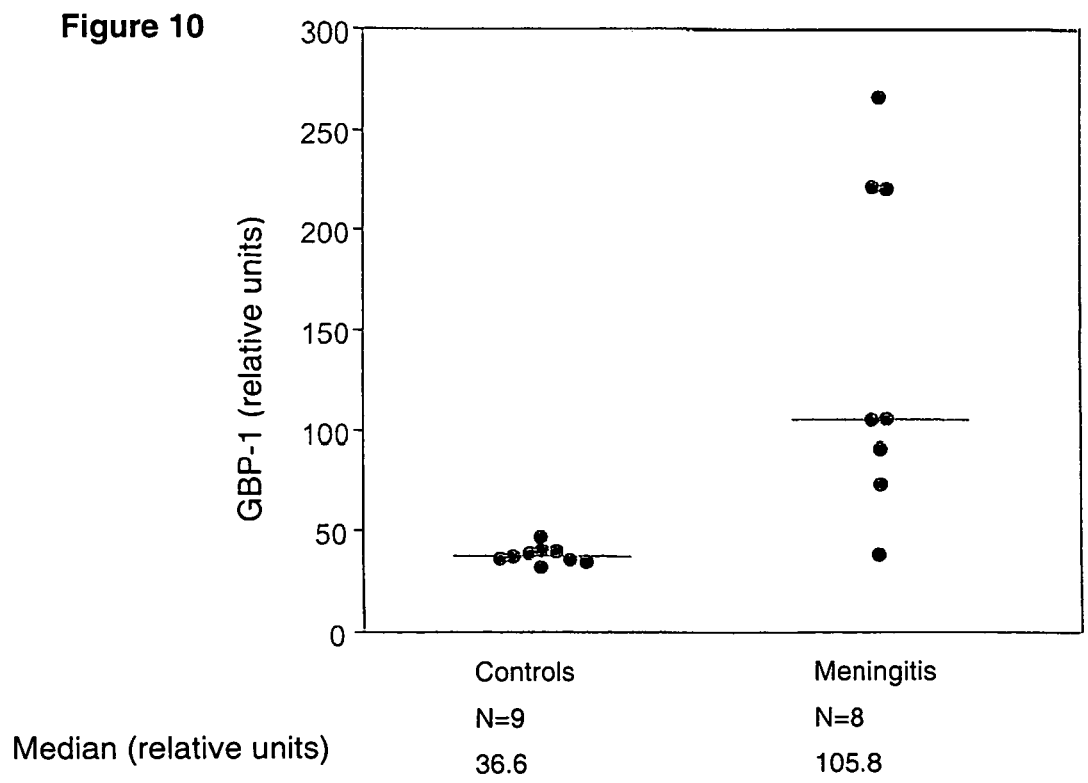

FIG. 10: Increased GBP-1 concentrations are detectable in the liquor of patients with bacterial meningitis In a blind test, the GBP-1 concentration was detected in 17 liquor samples by means of ELISA (FIG. 10). After deblinding the test it became obvious that significantly higher (Wilcoxon Test $p<0.03$) GBP-1 concentrations were detectable in the liquors (control persons=36.6 relative units and bacterial meningitis=105.8 relative units) in patients with bacterial (*Pneumokokkus, Staphylococcus aureus, Pseudomonas aeruginosa*) meningitis (n=8) as compared to healthy control persons (n=9). The GBP-1 liquor concentrations were determined as described. The liquor samples were diluted 1:2 in PBS. The concentration of GBP-1 in the sample was calculated by means of a standard curve. As the ELISA method also recognises GBP-2 and GBP-2 is possibly also present in the liquor, the concentrations determined were indicated in relative units.

The GBP-1 concentration in the liquor of healthy control persons showed no statically significant difference (Wilcoxon Test $p>0.05$) to the GBP-1 concentrations in the serum. This points to the fact that GBP-1 is not accumulated in the liquor of healthy persons and that the increase in GBP-1 concentrations in patients with meningitis is disease-induced.

The Examples illustrate the invention.

EXAMPLE 1

Production of a Vector Construct

The 237 bp GBP-1 promotor fragment (pro237-GBP-1) was generated by means of PCR amplification (PCR 2 Advantage Kit, Clontech) from the construct pro3757-GBP-1 with the oligonucleotides 5'-ATTTG<u>AAGCTT</u>CTGGTTGAG-3' (SEQ ID NO: 1)[insertion of a HindIII cleavage site (underlined)] or 5'-TGGCTTCTAGCACTTCTG-3' (SEQ ID NO: 2). The construct pro3757-GBP-1 contains 3757 bp of the 5' regulatory sequence upstream of the ATG condon of the GBP-1 gene (gi:4503938, NM_002053) in the vector pT-Adv (Clontech). The 237 bp fragment was ligated in antisense orientation with the vector pT-Adv, cleaved with HindIII and subcloned into the pGL3 Basic Vector (Promega). All constructs were purified by means of the Endofree Maxi Kit (Qiagen) and sequenced for verification.

EXAMPLE 2

Establishing a Suitable Cell Line

HEK 293 T-cells (human embryonic epithelial kidney cell line with human adenovirus type 5 (Ad 5) DNA-transformed (ATCC CRL 1573) which are additionally transformed with SV40 T antigen) were sewn with $3\times10^5$ cells/well (6-multi-well plate, Corning) 24 hrs prior to transfection. A total of 0.8 µg plasmid was used per well of the 6-well plate, with the test plasmid pro237-GBP-1 being used in a ratio of 1:5 with the selection plasmid pBABE-Puro (P. Monini, Laboratory of Virology, Insituto Superiore di Sanitá, Rome, Italy). The test plasmid pro237-GBP-1 contains the 237 bp promotor fragment linked to the indicator gene firefly-Luciferase, the selection plasmid pBABE-Puro, the resistance gene Puromycine, on which a selection is subsequently carried out. The transfection of the cells was carried out according to the producer's instructions with Effectene (Qiagen) and the selection was initiated after 24 hrs with 0.7 µg/ml Puromycine (Sigma). On days 8-10, the growth of the individual clones could be observed which were subsequently trypsinised with cloning rings and transferred in single wells of a 96-well plate (Falcon). At corresponding confluence, the clones were further passaged and were examined for their reporter gene activity in a luciferase assay. The clones were stimulated with inflammatory cytokines IFN-γ, IL-1β and TNF-α and buffer for 5 hrs and harvested in 1× passive lysis buffer (Promega). The lysates were examined for firefly-Luciferase activity and correspondingly stable clones were established.

EXAMPLE 3

Immunoprecipitation of GBP-1

Freshly prepared cell lysates were pre-purified by incubation with 2 µl rabbit pre-serum which does not react with GBP-1 and 25 µl protein A/G agarose beads for at least 3 hrs at 4° C. in a shaking platform. After pelleting the beads, the supernatant was incubated on a shaking platform with 25 µl protein A/G agarose beads and 1 µl polyclonal rabbit serum against GBP-1 over night at 4° C. The beads were washed four to five times in PBS. Subsequently, the beads were resuspended in 30 µl Laemmli sample buffer (2×) and boiled for 5 min. The samples were separated in an SDS-PAGE (10%) and analysed in a Western blot or in an autoradiography.

For the immunoprecipitation of GBP-1 or MMP-1 from cell culture supernatants, 10 ml culture medium were placed on ice, centrifuged at 1,000 rpm for 5 min, filtered by a filter with a mesh size of 45 µm and, in some cases, a proeinase inhibitor cocktail (0.02 mg/ml pancreas extract, 5 µg/ml pronase, 0.5 µg/ml thermolysin, 3 µg/ml chymotrypsin and 0.33 jm/ml papine) were added. The pre-purification was carried out by incubation with 10 µl rabbit serum and 120 µl protein A/G agarose beads at 4° C. for more than 3 hrs on a shaking platform. After pelleting the beads, the supernatant was incubated on a shaking platform with 120 µl protein A/G agarose beads and 6 µl polyclonal rabbit serum against GBP-1 at 4° C. over night. The beads were washed four to five times in PBS. Subsequently, the beads were resuspended in 60 µl PBS+60 µl Laemmli sample buffer (2×) and boiled for 5 min. Usually, 15 µl of each sample were separated in an SDS-PAGE (10%) and analysed in a Western blot.

FIG. 4B shows an example of the result of a detection of GBP-1 by immunoprecipitation from culture medium.

EXAMPLE 4

GBP-1 ELISA

The following buffers were used for the GBP-1 ELISA developed:

PBS containing 0.1% Tween 20 (PBS-T) and PBS containing 0.1% Tween 20 and 2% BSA (PBS-TB).

96-well ELISA plates (Nunc-Immuno Plates) were coated with 100 µl/well anti-GBP-1 hybridoma supernatant (diluted at a ratio of 1:5 with PBS) or with a purified receptor in the concentration of 1-5 µg/ml (incubation at 4° C. for 16 hrs). The plates were washed with PBS-T and blocked with PBS-TB for at least 30 min. at room temperature. The wells were sucked off and were incubated as duplicates for 2 hrs at room temperature with 100 µl of the standard (GBP-1-His), diluted in a cell culture medium containing 5% FBS), the same concentration of BSA as control or with 100 µl of a sample at a suitable dilution (diluted with PBS). The wells were washed four times with PBS-T and were incubated with 100 µl of a polyclonal antibody against GBP-1, diluted in 1:500 in PBS-TB for 2 hrs at room temperature. Subsequently, the wells were washed four times with PBS-T and incubated with 100 µl of an alkaline phosphatase which is conjugated to a rabbit antibody (Zymed, Berlin, Germany), diluted 1:500 in PBS-TB, for 1 h at room temperature. Subsequently, the wells were washed four times with PBS-T and were incubated with 100 µl p-nitrophenyl phosphate (Zymed). The absorption was determined at 405 nm in a micro plate reader (BioRad). The concentration of GBP-1 in the sample was calculated by means of the standard curve. The method showed a linearity of 0.1 to 100 ng/ml of GBP-1/well. The variability of the results in the different assays was between 2.3 and 6%.

An example of the result of the detection of GB-1 in the culture supernatant by ELISA is shown in FIG. 4A.

The sensitivity of the ELISA was determined in PBS by means of a dilution series of GBP-1-His (a GBP-1 protein which was purified from bacteria and to which 6 histidine residues were added at the carboxy terminus for purification).

The sensitivity of the ELISA was fixed as the lowest concentration of GBP-1-His at which the corresponding measuring value differed significantly, i.e. by at least two standard deviations, from the measuring value which was obtained in the assay without GBP-1-His (plus two standard deviations). In this respect, the sensitivity of the ELISA described herein was determined as 12.3 ng/ml.

1. Intra-assay Variability:

The reproducibility of the results within a test was determined by threefold measurements. Thus, the variability was calculated as follows:

Variability=(standard deviation/mean value)×100%.

By adding GBP-1-His to the serum (1:2 diluted in PBS) of a healthy proband, three test solutions with different GBP-1-His concentrations (400 ng/ml, 180 ng/ml, 40 ng/ml) were produced. The intra-assay variability was determined with each solution:

GBP-1-His 400 ng/l; intra-assay variability=2.7%
GBP-1-His 180 ng/l; intra-assay variability=2.8%
GBP-1-His 40 ng/l; intra-assay variability=2.0%

2. Inter-assay Variability:

The reproducibility of the ELISA was determined in different tests in order to determine the inter-assay variability. To this avail, each of the above-indicated solutions was measured six times. The inter-assay variability was calculated as described above.
GBP-1-His 400 ng/l; intra-assay variability=4.4%
GBP-1-His 180 ng/l; intra-assay variability=2.8%
GBP-1-His 40 ng/l; intra-assay variability=3.0%

LITERATURE

Carmeliet. and Jain: Nature 407(6801): 249-57 (2000).
Folkman: Nat Med 1(1): 27-31 (1995).
Guenzi, Töpolt, Cornali, Lubeseder-Martellato, Jörg, Matzen, Zietz, Kremmer, Nappi, Schwemm/e, Hohenadl, Barillari, Tschachler, Monini, Ensoli, and Stürzl: (2001) EMBO J 20(20): 5568-77.
Guenzi E, Töpolt K, Lubeseder-Martellato C, Jörg A, Naschberger E, Benelli R, Albini A, Stürzl M: (2003) The guanylate binding protein-1 GTPase controls the invasive and angiogenic capability of endothelial cells through inhibition of MMP-1 expression. EMBO J. 22(15):3772-82
Harlow und Lane, "Antibodies, a laboratory manual", CSH Press 1988, Cold Spring Harbor
Töpolt, Guenzi, Lubeseder-Martellato, Jörg, Naschberger, Sturzl: Proceedings of the 22nd Meeting of the European Society of Microcirculation (2002).
Lubeseder-Martellato, Guenzi, Jörg, Töpolt, Naschberger, Kremmer, Zietz, Tschachler, Hutzler, Schwemmle, Matzen, Grimm, Ensoli and Stürzl: Am J Pathol 161(5): 1749-59 (2002).
Prakash, Praefcke, Renault, Wittinghofer and Herrmann: Nature 403(6769): 567-71 (2000).

The invention claimed is:

1. An in-vitro method for identifying guanylate binding protein-1 in a sample comprising:
 (a) contacting a sample of a supernatant of a tissue culture, a sample of a supernatant of a cell culture or a sample of a body fluid with a first antibody which specifically binds guanylate binding protein-1; and
 (b) detecting a specific binding of the antibody with guanylate binding protein-1; and
thereby identifying the presence of guanylate binding protein-1 in the supernatant of said tissue culture, the supernatant of said cell culture sample or body fluid sample.

2. The method according to claim 1, wherein the antibody is immobilized on a surface prior to contacting with said sample.

3. The method according to claim 1, wherein the antibody is immobilized on a surface after contacting with said sample.

4. The method according to claim 2 or 3 wherein the material of the surface is selected from the group consisting of sepharose, latex, glass, polystyrene, polyvinyl, nitrocellulose and silicon.

5. The method according to claim 2 or 3, wherein the surface is a membrane, a bead, a chip or a plate.

6. The method according to claim 5, wherein the surface is a bead and further comprising, prior to step (b):
 (a''') allowing formation of any complexes between the sample and antibody on the beads and precipitating the beads with complexes that are bound to said beads.

7. The method according to claim 1, wherein the detection of the specific binding in step (b) comprises a gel electrophoretic separation.

8. The method according to claim 1, wherein for the detection of a specific binding of said guanylate binding protein-1 with the first antibody in step (a), the sample is contacted with a second antibody specific for guanylate binding protein-1 which binds to an epitope of guanylate binding protein-1 that is accessible after the binding of the first antibody to said guanylate binding protein-1.

SEQUENCE LISTING

<160> NUMBER OF SEQ ID NOS: 2

<210> SEQ ID NO 1
<211> LENGTH: 20
<212> TYPE: DNA
<213> ORGANISM: Artificial sequence
<220> FEATURE:
<221> NAME/KEY:
<223> OTHER INFORMATION: primer

<400> SEQUENCE: 1
atttgaagct tctggttgag                                        20

<210> SEQ ID NO 2
<211> LENGTH: 18
<212> TYPE: DNA
<213> ORGANISM: Artificial sequence
<220> FEATURE:
<221> NAME/KEY:
<223> OTHER INFORMATION: primer

<400> SEQUENCE: 2
tggcctctag cacttctg                                          18

9. The method according to claim 8, wherein the second antibody is labeled.

10. The method according to claim 9, wherein the label of the second receptor for guanylate binding protein-1 or fragment of guanylate binding protein-1 comprises a system emitting a signal.

11. The method according to claim 10, wherein the system emitting a signal comprises an enzyme emitting the signal.

12. The method according to claim 1, wherein the method is an ELISA, an EIA or a RIA.

13. The method according to claim 1, wherein the method is carried out automatically.

14. The method according to claim 1, wherein said antibody is a polyclonal antibody.

15. The method according to claim 1, wherein said antibody is a monoclonal antibody.

16. The method according to claim 1, wherein the amount of identified guanylate binding protein-1 is quantified.

17. The method according to claim 1, wherein said tissue comprises endothelial cells.

18. The method according to claim 1, wherein said body fluid is human serum, human plasma or human liquor.

19. The method according to claim 1, wherein said cell culture comprises endothelial cells.

20. The method according to claim 7, wherein said detection step comprises a Western blot.

21. The method according to claim 9, wherein the label on said second antibody is specifically recognized by a third antibody comprising a system emitting a signal.

\* \* \* \* \*